(12) United States Patent
Bombardelli et al.

(10) Patent No.: US 6,683,109 B2
(45) Date of Patent: Jan. 27, 2004

(54) CONDENSATION DERIVATIVES OF THIOCOLCHICINE AND BACCATIN AS ANTITUMOR AGENTS

(75) Inventors: Ezio Bombardelli, Milan (IT); Alessandro Pontiroli, Milan (IT)

(73) Assignee: Indena S.p.A., Milan (IT)

( * ) Notice: Subject to any disclaimer, the term of this patent is extended or adjusted under 35 U.S.C. 154(b) by 0 days.

(21) Appl. No.: 10/210,134

(22) Filed: Aug. 2, 2002

(65) Prior Publication Data

US 2003/0073734 A1 Apr. 17, 2003

Related U.S. Application Data

(63) Continuation of application No. PCT/EP01/02740, filed on Mar. 21, 2001.

(30) Foreign Application Priority Data

Mar. 17, 2000 (IT) .................................. MI2000A000553

(51) Int. Cl.⁷ .................... C07D 305/14; A61K 31/337
(52) U.S. Cl. .................... 514/449; 549/510; 549/511
(58) Field of Search ................. 549/510, 511; 514/449

(56) References Cited

U.S. PATENT DOCUMENTS 5,426,224 A * 6/1995 Lee et al. ................... 564/177

FOREIGN PATENT DOCUMENTS

| WO | WO 93/02105 | * | 2/1993 |
| WO | WO 93/11120 | * | 6/1993 |
| WO | WO 97/24459 | * | 7/1997 |

OTHER PUBLICATIONS

S.–X Zhang et al., "Antitumor Agents. 199. Three–Dimensional Quantitative Structure —Activity Relationship Study of the Colchicine Binding Site Ligands Using Comparative Molecular Field Analysis," J. Med. Chem. 2000, 43:2, pp. 167–176, 2000.*

* cited by examiner

Primary Examiner—Ba K. Trinh
(74) Attorney, Agent, or Firm—Pennie & Edmonds LLP

(57) ABSTRACT

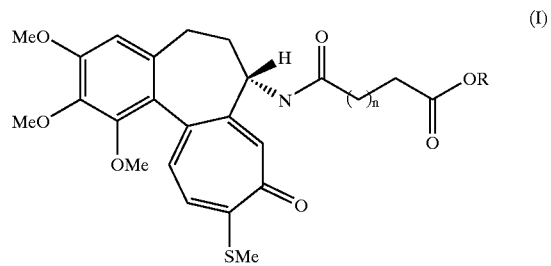

N-deacetyl-thiocolchicine and 10-deacetyl-baccatin III derivatives of formula (I) wherein R and n have the meanings specified in the disclosure, are valuable antitumoral drugs.

18 Claims, No Drawings

CONDENSATION DERIVATIVES OF THIOCOLCHICINE AND BACCATIN AS ANTITUMOR AGENTS

This application is a continuation of PCT/EP01/02740 dated Mar. 12, 2001.

FIELD OF THE INVENTION

The present invention relates to derivatives of N-deacetyl-thiocolchicine and 10-deacetyl-baccatin III derivatives of formula (I)

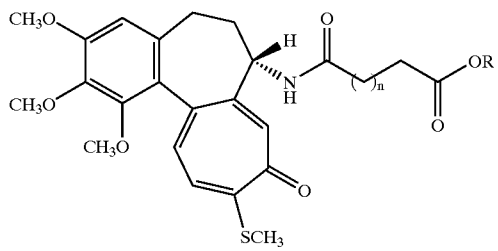

wherein:

n is an integer of 0 to 8;

R is a residue of formula a), b), c), d) or e):

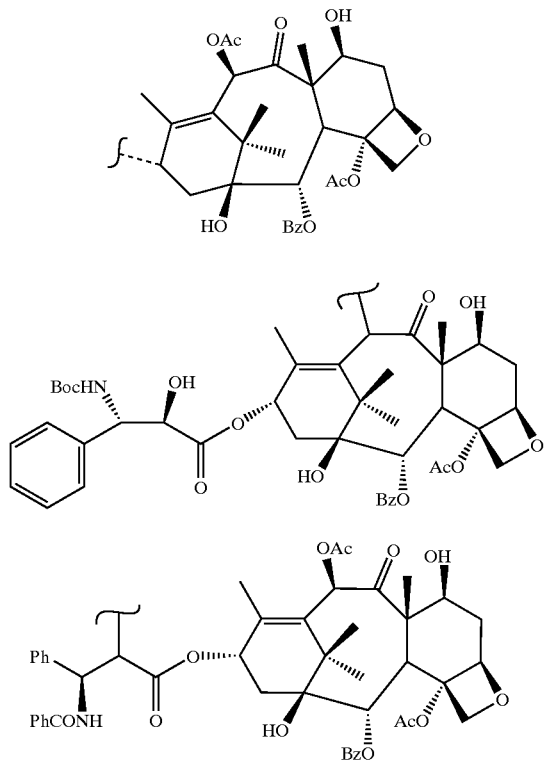

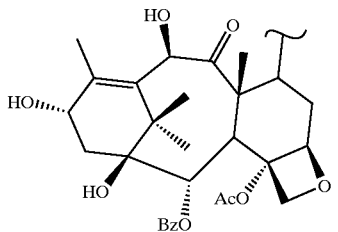

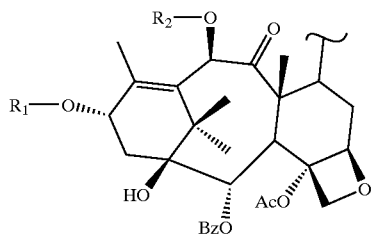

wherein:

$R_1$ and $R_2$, which can be the same or different, are hydrogen or a group of formula:

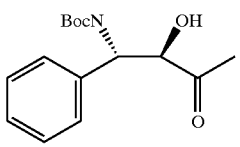

n is preferably an integer of 1 to 7, more preferably 1.

TECHNICAL FIELD

Colchicines and thiocolchicines are known antiblastic compounds capable of destabilizing microtubules through interaction with tubulin Colchicine is currently used in the therapy of gout and related inflammatory conditions, but its use is restricted to the acute phases due to its high gastro-intestinal toxicity.

A number of colchicine or thiocolchicine derivatives have been studied, in view of a possible use thereof as antitumor medicaments, but the efforts of researchers have to date been unsuccessful due to the often very restricted therapeutical index of such compounds.

Only one colchicine derivative, demecolcine, has been used in the past in clinic for the treatment of leukemias, but with poor success.

The antiproliferative activity of taxane derivatives (paclitaxel and derivatives) is related to the capability of irreversibly binding to the alpha and beta forms of tubulin in the microtubule as well. The oxethane and the phenyl groups on the isoserine side chain proved to be essential as regards activity: baccatine in fact, lacking the isoserine chain, has substantially no antiproliferative activity, contrary to paclitaxel and other $C_{13}$ esters of isoserine, which can form bonds with two different sites of the microtubule preventing depolymerization hence arresting the activity of the mitotic spindle.

SUMMARY OF THE INVENTION

It has now surprisingly been found that compounds of formula (I) have anti-proliferative activity, although lacking affinity to tubulin, both in the microtubules assembling and disassembling steps.

DETAILED DESCRIPTION OF THE PREFERRED EMBODIMENTS

The activity of the compounds of formula (I) is therefore due to an unexpected action mechanism that cannot be evinced from the present knowledge in the anti-tubuline drug field.

The compounds of the invention have powerful antimitotic activity and are characterized by favorable therapeutic index which makes them suitable for the therapeutical treatment of various forms of tumors, as well as for degenerative rheumatoid arthritis, a disease characterized by excessive proliferation and abnormal migration of leukocytes.

Compounds (I) have cytotoxicity comparable to that of the most effective antitumor medicaments, while having a remarkably wider action spectrum, particularly against cells resistant to known drugs.

Compounds (I) are prepared by reacting N-deacetyl-thiocolchicine with dicarboxylic acid reactive derivatives in dry solvents in such conditions as to obtain a N-monoacylation product which is subsequently reacted with the baccatine III derivative, optionally protected at the 7, 13 or 10 positions, depending on the desired compound, in the presence of a suitable condensing agent, such as dicyclohexylcarbodiimide. Any protective groups optionally present are removed and/or the hydroxy groups on the baccatine III residue are selectively acylated to directly yield compounds (I).

When in compounds (I) R is a group of formula c), thanks to the reactivity of the hydroxy group in the isoserine chain, the reaction can be carried out without previously protecting the other hydroxy groups present on the taxane compound.

Examples of suitable dicarboxylic acid reactive derivatives comprise acyl halides, acid chlorides, reactive anhydrides or esters.

Alternatively, a taxane derivative can also be acylated with a dicarboxylic acid and the resulting product be condensed with N-deacetyl-thiocolchicine.

The compounds of the invention are useful in the treatment of proliferative pathologies and in particular tumors of various origins, rheumatoid arthritis or other degenerative pathologies wherein antiproliferative and anti-inflammatory actions are indicated.

For this purpose, compounds (I) will be administered in the form of pharmaceutical compositions suitable to the oral, parenteral, epicutaneous or transdermal administrations. The dosage of compounds (I) will range from 1 to 100 mg/m$^2$ body area, depending on the administration route. The compounds will preferably be administered orally.

Examples of compositions comprise capsules, tablets, vials, creams, solutions, granulates.

The following examples illustrate the invention in greater detail.

EXAMPLE 1 a) 100 mg of deacetylthiocolchicine (0.268 mmol, M.W. 373 g/mol) are dissolved in 5 ml of dry dioxane, then added with 27 mg of succinic anhydride (0.268 mmol, M.W. 100 g/mol) and the reaction mixture is heated to 60° C. for 5 hours. TLC control: AcOEt/MeOH 4:1. Dioxane is evaporated off and the product is used without purification for the subsequent reaction. 130 mg of product are obtained.

b) 126 mg of the product from step a) (0.268 mmol, M.W. 473 g/mol) are dissolved in 8 ml of dry toluene. 187 mg of 7-Tes-Baccatine (0.268 mmol, M.W. 700 g/mol), 66 mg of DCC (0.321 mmol, M.W. 206 g/mol) and 13 mg of DMAP (0.1 mmol, M.W. 122 g/mol) are added. The mixture is stirred at room temperature for about 12 hours until disappearance of the starting products. TLC control: AcOEt/MeOH 4:1. The mixture is filtered through Celite and evaporated to dryness. The crude is purified on a column (silica gel) using AcOEt/hexane 9:1 as eluent, to obtain 120 mg of the protected condensation product and 80 mg of the product already 7-deprotected.

c) 120 mg of the product from step b) (0.103 mmol, M.W. 1155 g/mol) are dissolved in 5 ml of MeOH/AcCl (5 ml of methanol and 35 μl of AcCl). The reaction is completed within 15 minutes. The mixture is added with bicarbonate and extracted with AcOEt, to obtain 100 mg of a product of formula (I), wherein n is 1 and R is a residue of formula a).

EXAMPLE 2 a) 100 mg of 10-O-succinyl-7-Tes-baccatine III (M.W. 699 g/mol, 0.14 mmol) and 54 mg of N-deacetylthiocolchicine (M.W. 373 g/mol, 0.14 mmol) are dissolved in 5 ml of dry toluene added with 2 ml of methylene chloride. 31 mg of DCC (M.W. 206 g/mol, 0.15 mmol) and 8.5 mg of DMAP (M.W. 122 g/mol, 0.07 mmol) are added at room temperature. After one day, the reaction is filtered through Celite, washed with toluene and evaporated to dryness. Purification on a flash column (silica gel eluent CH$_2$Cl$_2$; MeOH=25:1) yields 70 mg of product.

b) 200 mg of the product from step a) (0.213 mmol) are dissolved in 14 ml of dry toluene. 183 mg of the oxazolidine derivative of formula:

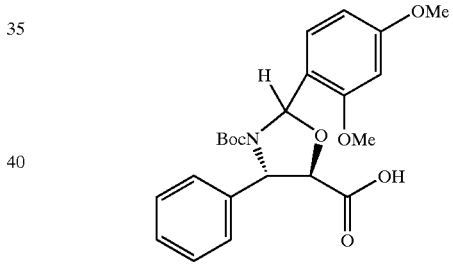

SHA 9 in the following referred to as SHA-9, (0.426 mmol), 88 mg of DCC (0.426 mmol) and 26 mg of DMAP (0.213 mmol) are added and the mixture is stirred at room temperature. TLC control: CH$_2$Cl$_2$; MeOH=25:1. After 4 hours the reaction mixture is filtered through Celite and purified by column chromatography, to obtain 240 mg of product.

c) 160 mg of the product from step b) (0.12 mmol M.W. 1338) are dissolved in 3.2 ml of a solution obtained dissolving 70 μl of AcCl in 10 ml of MeOH. After half an hour the reaction mixture is added with 5% NaHCO$_3$, extracted with CH$_2$Cl$_2$, dried and the solvent is evaporated off. Purification by flash chromatography yields 97 mg of the compound (I) wherein n is 1 and R is a residue of formula b).

EXAMPLE 3

70 mg of paclitaxel (0.038 mmol, M.W. 1824) are dissolved in 5 ml of dry dioxane. DCC (1.5 eq.), DMAP (5% in mols) and the product of example 1a are added. The mixture is stirred at 110° C. for 2 h, then added with a further 10 mg of the product of example 1a and 11 mg of DCC. Afterwards, the reaction is left at room temperature for 48 hours, then heated at 110° C. for a further 24 hours. The solvent is evaporated off and the residue is purified by flash chromatography (AcOEt: MeOH=99:1) to obtain 21 mg of compound (I) wherein n is 1 and R is a residue of formula c).

EXAMPLE 4 a) A solution of 7-succinyl, 10,13-di-Tes-baccatine III (390 mg, 0.479 mmol, M.W. 814) in 10 ml of THF is added with a solution of TBAF (1M in THF, 0.96 mmol) at 0° C. The mixture is left for 1 h 30 min. at 0° C., then for 2 h at room temperature. After that, 1 eq of TBAF is added and the reaction is continued until complete elimination of the protective groups. The reaction mixture is added with water and extracted with AcOEt; the aqueous phase is acidified with 1N HCl and extracted with AcOEt, to obtain 350 mg of product.

b) The compound from step a) (0.479 mmol) is reacted with TIO-NH$_2$ (0.479 mmol), DCC (1.5 eq.) and DMAP (50% by mol) in toluene-THF for 1 hour. The reaction mixture is filtered through Celite and purified by CC (CH$_2$Cl$_2$: MeOH=25:1), to obtain compound (I) wherein n is 1 and R is a residue of formula d).

EXAMPLE 5

200 mg of the compound of example 4 (0.206 mmol) are dissolved in 14 ml of toluene—dry THF. 177 mg of SHA 9 (2 eq.), 84 mg of DCC (2 eq.) and 26 mg of DMAP (0.206 mmol) are added to the mixture, which is stirred at room temperature. TLC control: CH$_2$Cl$_2$: MeOH=25:1. After 4 hours the reaction mixture is filtered through Celite and purified on a chromatographic column. The resulting product is dissolved in 4.8 ml of a solution of 70 µl of AcCl in 10 ml of MeOH. After half an hour the reaction is added with 5% NaHCO$_3$ and extracted with CH$_2$Cl$_2$. The extract is dried and the solvent is evaporated off. The residue is purified by flash chromatography to obtain 110 mg of compound (I) wherein n is 1, R is a residue of formula e) wherein R$_1$ and R$_2$ are groups of formula

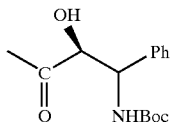

What is claimed is:

1. A compound of formula:

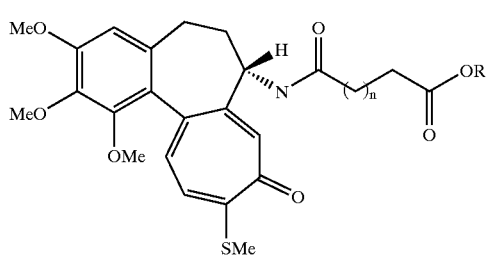

wherein:

n is 0 or an integer from 1 to 8;

R is a residue of formula

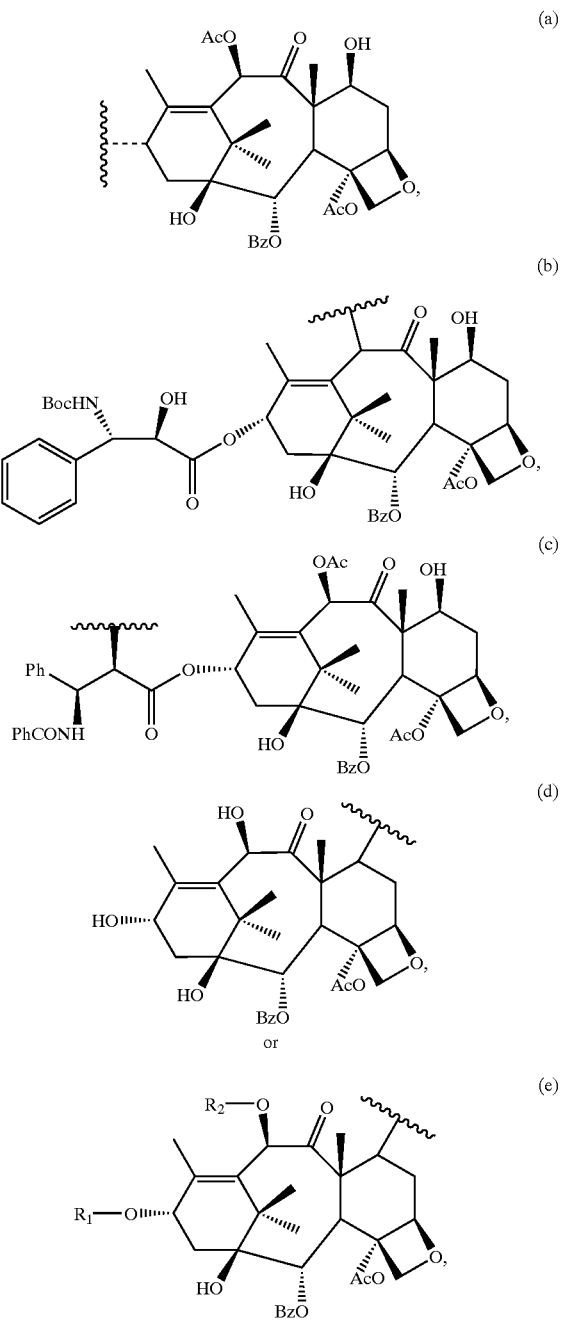

wherein R$_1$ and R$_2$ are each independently hydrogen or a group of formula

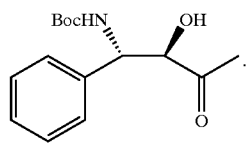

2. The compound of claim 1, wherein n is an integer from 1 to 7.

3. The compound of claim 2, wherein n is 1.

4. A pharmaceutical composition comprising the compound of claim 1 and a pharmaceutically acceptable excipient.

5. The pharmaceutical composition of claim 4 in the form of a capsule, tablet, cream, solution, or granulate.

6. A pharmaceutical composition comprising the compound of claim 2 and a pharmaceutically acceptable excipient.

7. The pharmaceutical composition of claim 6 in the form of a capsule, tablet, cream, solution, or granulate.

8. A pharmaceutical composition comprising the compound of claim 3 and a pharmaceutically acceptable excipient.

9. The pharmaceutical composition of claim 8 in the form of a capsule, tablet, cream, solution, or granulate.

10. A method for treating tumors or degenerative rheumatoid arthritis in a patient comprising administering to the patient a therapeutically effective amount of a compound of claim 1.

11. The method of claim 10, wherein the therapeutically effective amount is from 1 to 100 mg/m$^2$ of body area.

12. The method of claim 10, wherein the therapeutically effective amount is administered orally.

13. A method for treating tumors or degenerative rheumatoid arthritis in a patient comprising administering to the patient a therapeutically effective amount of a compound of claim 2.

14. The method of claim 13, wherein the therapeutically effective amount is from 1 to 100 mg/m$^2$ of body area.

15. The method of claim 13, wherein the therapeutically effective amount is administered orally.

16. A method for treating tumors or degenerative rheumatoid arthritis in a patient comprising administering to the patient a therapeutically effective amount of a compound of claim 3.

17. The method of claim 16, wherein the therapeutically effective amount is from 1 to 100 mg/m$^2$ of body area.

18. The method of claim 16, wherein the therapeutically effective amount is administered orally.

* * * * *